United States Patent
Kossmehl et al.

[11] Patent Number: 4,849,520
[45] Date of Patent: Jul. 18, 1989

[54] FUSIBLE, ELECTRICALLY CONDUCTIVE TCNQ COMPLEXES, METHODS FOR THEIR PREPARATION AND THEIR APPLICATION

[75] Inventors: Gerhard Kossmehl; Detlef Kabbeck-Kupijai, both of Berlin; Friedrich Jonas, Aachen, all of Fed. Rep. of Germany

[73] Assignee: Bayer Aktiengesellschaft, Leverkusen, Fed. Rep. of Germany

[21] Appl. No.: 84,659

[22] Filed: Aug. 11, 1987

[30] Foreign Application Priority Data

Aug. 26, 1986 [DE] Fed. Rep. of Germany ....... 3628905

[51] Int. Cl.$^4$ ............................................ C07D 213/20
[52] U.S. Cl. .................................................... 546/347
[58] Field of Search .......................................... 546/347

[56] References Cited

U.S. PATENT DOCUMENTS

| | | | |
|---|---|---|---|
| 3,115,506 | 12/1963 | Acker et al. | 546/264 |
| 3,941,792 | 3/1976 | Murakami | 546/182 |
| 4,580,855 | 4/1986 | Niwa | 252/62.6 |

OTHER PUBLICATIONS

Melby et al., *J. Am. Chem. Soc.*, vol. 84, (1962), pp. 3374–3387.

*Primary Examiner*—Mary C. Lee
*Assistant Examiner*—Zinna Northington
*Attorney, Agent, or Firm*—Sprung Horn Kramer & Woods

[57] ABSTRACT

The invention relates to fusible, electrically conductive N-arylpyridinium-TCNQ complexes of the formula

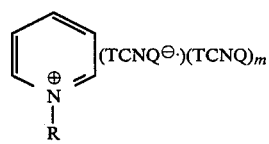

(II)

in which
m is zero or an integer from 0 to 2 and
R represents an optionally substituted aryl radical, and their use for preparing conductive coatings on substrates.

2 Claims, No Drawings

FUSIBLE, ELECTRICALLY CONDUCTIVE TCNQ COMPLEXES, METHODS FOR THEIR PREPARATION AND THEIR APPLICATION

The invention relates to new fusible, electrically conductive complex salts of 7,7,8,8-tetracyano-p-quinodimethane (TCNQ).

Complex salts of TCNQ and their use as electrically conductive compounds are known (see, e.g., J. Am. Chem. Soc. vol. 84 (1962), pages A3374–3387; U.S. Pat. Nos. 3,941,792 and 4,580,855 and deutsche Offenlegungsschrift (German Published Specification) No. 3,417,466). These complex salts correspond to the general formula

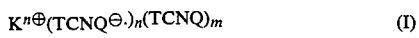

$$K^{n\oplus}(TCNQ^{\ominus}\cdot)_n(TCNQ)_m \qquad (I)$$

in which $K^{n+}$ indicates a cation and n indicates an integer corresponding to the valency of K, and m indicates the number of moles of neutral TCNQ which is contained in a mole of the complex salt; the following applies for m: $0 \leq m \leq 2n$, preferably $0 \leq m \leq n$.

Hitherto alkali-metal and alkaline earth metal ions, and furthermore arsonium, phosphonium and ammonium ions have been proposed as $K^{n\oplus}$ cations. As ammonium ions, use was primarily made of those which are derived from tertiary amines, such as trialkylamines, dialkylanilines and pyridines, and quaternary ammonium compounds, such as quinolinium, isoquinolinium and pyridinium compounds or else N-alkyl derivatives thereof.

Of the TCNQ complexes known hitherto, the salts of the formula (I), in which $K^{n\oplus}$ represents a ammonium ion, for example, a (N-alkyl-)pyridinium-, (N-alkyl-)quinolinium-, (N-alkyl-)isoquinolinium ion or a phosphonium ion are fusible. These fusible complexes have, however, the disadvantage that their electrical conductivity decreases by several powers of ten when they melt (N-alkylpyridinium-TCNQ complexes, such as the N-methylpyridinium-TCNQ complex) or that, although they are stable for a short time in the melt, they do not have, on the other hand, an electrical conductivity which is adequate for many fields of application (isoquinolinium-TCNQ complexes).

Surprisingly, it has now been found that TCNQ complexes of the formula (I), in which $K^{n\oplus}$ represents an N-arylpyridinium ion, have not only a favourable melt behaviour and a high thermal stability, but also, at the same time, an excellent electrical conductivity.

The invention therefore relates to TCNQ complexes of the formula

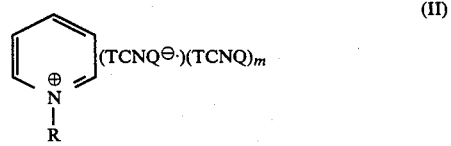

(II)

in which m is zero or an integer or a fractional number from 0 to 2, preferably from 0 to 1, and R represents an optionally substituted aryl radical.

For R mononuclear and polynuclear aryl radicals, preferably optionally substituted phenyl and naphthyl radicals, are suitable as aryl radicals.

As substituents for said aryl radicals mention may be made, for example, of $C_1-C_{20}$-, preferably $C_1-C_4$-alkyl groups, $C_1-C_{20}$-, preferably $C_1-C_4$-alkoxy groups, halogen atoms, in particular, chlorine, bromine or iodine atoms, nitro groups, nitrile groups, $C_1-C_{20}$-, preferably $C_1-C_5$-acyl groups, and furthermore carboxylic ester groups.

Examples of such optionally substituted phenyl and naphthyl radicals are, for example: the phenyl, tolyl, cresyl and tert-butylphenyl radicals; the 1-naphthyl and 2-naphthyl radical; furthermore, the ethoxyphenyl, nitrophenyl, acetylphenyl, cyanophenyl and chlorophenyl radical. Preferably, R represents a phenyl radical or a phenyl radical substituted by $C_1-C_4$-alkyl, $C_1-C_4$-alkoxy, $C_1-C_5$-acyl radicals and/or halogen atoms.

The novel TCNQ complexes of formula (II) may be prepared by methods known per se, e.g., the methods described in J. Am. Chem. Soc. 84, (1962), pages 3374 et seq., in particular on page 3380. One of these methods proceeds according to the following reaction equation

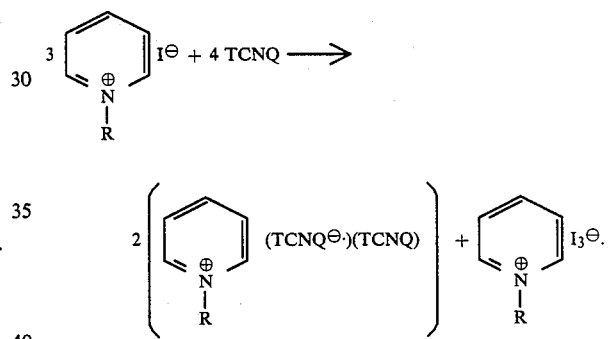

The reaction of the N-arylpyridinium iodides with TCNQ is performed preferably in organic solvents at temperatures below 150° C., preferably at temperatures from 20° to 100° C.

Suitable solvents for this reaction are, e.g., halogenated hydrocarbons, e.g. methylene chloride, chloroform, tetrachloromethane, 1,2-dichloroethane, 1,1,2-trichloroethane; acetonitrile; alcohols, e.g. methanol, ethanol, isopropanol; aliphatic ketones, e.g. acetone, methyl ethyl ketone; acyclic or cyclic ethers, e.g. diethyl ether, tetrahydrofuran. The reactants, TCNQ and N-arylpyridinium iodides, are used in a molar ratio of 1:0.5–1.5.

Another method proceeds according to the following reaction equation (X=anion, preferably halide ion; M=metal ion, preferably $Li^{\oplus}$):

Stage 1:

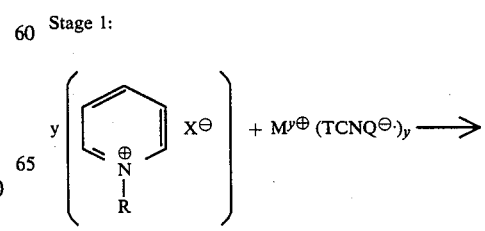

-continued

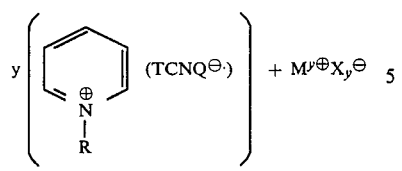 + $M^{y\oplus}X_y^{\ominus}$

Stage 2:

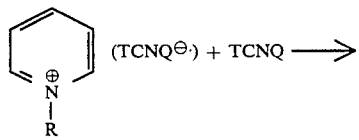

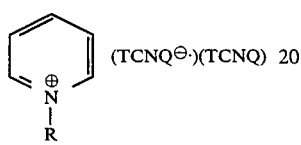

In stage 1, the reaction is performed preferably in aqueous alcohols, in stage 2 preferably in acetonitrile.

Because of their favourable melt behaviour and their high thermal stability, the novel N-arylpyridinium-TCNQ complexes of the formula (II) are suitable particularly for the preparation of electrically conducting coatings on substrates produced by melting-on.

The invention therefore relates also to the use of the novel N-arylpyridinium-TCNQ complexes for preparing electrically conductive coatings produced by melting-on on substrates or else by dip-coating substrates.

The novel TCNQ complexes can also be processed into conducting coatings from the melt. These coatings may optionally contain also stabilizing additives which improve adhesion or impart colour, or lower the melting point.

As substrates suitable for coating, mention may be made of, for example, glass, metals, metal oxides, such as aluminium oxide, and furthermore organic polymers.

The coating of the substrates may be formed in a manner such that the substrates are heated to a temperature above the melting point of the N-arylpyridinium-TCNQ complexes and then the solid TCNQ complexes are sprinkled on said hot substrate surfaces. This melting-on of the TCNQ complexes onto the heated substrate surfaces may be performed optionally in a protective gas atmosphere, e.g. under hydrogen, nitrogen, argon or helium, or else in vacuo.

In another method, the procedure is to apply the TCNQ complexes of formula (II) to the substrates to be coated at room temperature and then to melt them on in a preheated furnace.

A third method of application is to coat the substrates by dipping in a melt of the TCNQ complexes of the formula (II).

All of these methods result in electrically conductive coatings on the substrates. The substrates so prepared and provided with an electrically conductive coatings are used in the electronics industry.

The novel N-arylpyridinium-TCNQ complexes are suitable also for incorporation in plastic materials, e.g. in polycarbonates, to render them antistatic.

EXAMPLE 1

A suspension of 8.2 g (0.04 mol) of TCNQ in 200 ml of acetonitrile is added to a solution of 8.5 g (0.03 mol) of N-phenylpyridinium iodide in 50 ml of acetonitrile at reflux temperature while stirring. The mixture is then stirred for a further 10 minutes at reflux temperature.

During cooling, a crystalline precipitate deposits from the solution. This is filtered by suction after standing for 12 hours, washed with a little acetonitrile and dried.

Yield: 7.9 g (70% of theory) of the N-phenylpyridinium-TCNQ complex of the formula

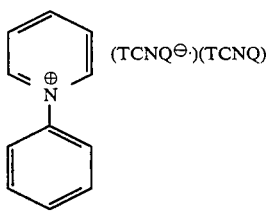

Determination of the melt behaviour and the thermal stability of various TCNQ complexes and of the N-phenylpyridinium-TCNQ complex described above:

In each case 0.5 g of TCNQ complex are melted for 1 minute at the temperature T specified in the table below. The conductivities of the various TCNQ complexes before melting ($\sigma^o$) and of the resolidified melt ($\sigma^s$) are determined (four-electrode measurement at a pressure of 250 kgf/cm²).

The table below summarizes the various TCNQ complexes investigated, the temperatures required to melt them and the $\delta^o$ (sic) and $\delta^s$ values obtained.

TABLE

| $K^{\oplus}$ | T (°C.) | $\sigma^o$(S/cm) | $\sigma^s$(S/cm) |
|---|---|---|---|
| 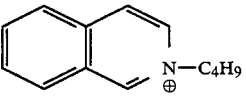 | 250 | 0.1 | 0.08 |
| (according to DE-OS (German Published Specification) 3,214,355) | | | |
| 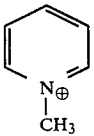 | 280 | $5 \times 10^{-3}$ | $10^{-7}$ |
| (according to DE-OS (German Published Specification) 2,329,492) | | | |
| 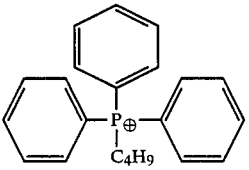 | 230 | $7 \times 10^{-3}$ | $4 \times 10^{-3}$ |
| (according to DE-OS (German Published Specification) 3,417,466) | | | |

TABLE-continued

| K⊕ | T (°C.) | $\sigma^o$(S/cm) | $\sigma^s$(S/cm) |
|---|---|---|---|
|  | 280 | 0.5 | 0.3 |

(according to Example 1)

EXAMPLE 2

The boiling solution of 1.42 g (6.7 mmol) of Li⊕(TCNQ⊖) in 20 ml of aqueous methanol (CH$_3$OH:H$_2$O=10:1) is added to the solution of 2.0 g (6.8 mmol) of N-p-tolyl-pyridinium iodide in 13 ml of aqueous methanol (CH$_3$OH:H$_2$O=10:1). The mixture is heated at reflux temperature for 10 minutes.

After cooling, the precipitate is filtered off by suction, washed with a little cold water and dried.

Yield: 2.14 g (85% of theory) of the N-p-tolyl-pyridinium-TCNQ complex of the formula

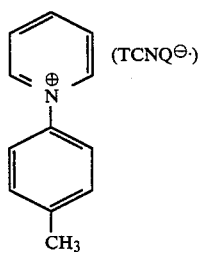 (TCNQ⊖·)

The 2.14 g (5.7 mmol) of N-p-tolylpyridinium-TCNQ salt are heated with 1.16 g (5.7 mmol) of TCNQ in 100 ml of acetonitrile for 10 minutes at reflux temperature. After cooling, the crystalline precipitate is filtered off by suction, washed with a little cold acetonitrile and dried.

Yield: 2.89 g (87% of theory) of the N-p-tolyl-pyridinium-TCNQ complex of the formula

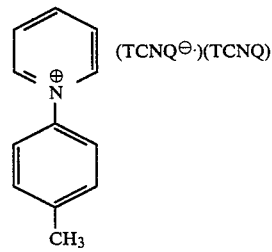 (TCNQ⊖·)(TCNQ)

What is claimed is:

1. A pyridinium-TCNQ complex of the formula

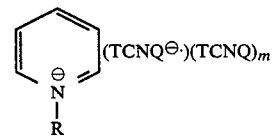 (TCNQ⊖·)(TCNQ)$_m$ in which
m is zero or an integer or a fraction number from 0 to 2, and
R represents an unsubstituted phenyl or naphthyl radical or a phenyl or naphthyl radical which is substituted by C$_1$–C$_{20}$-alkyl, C$_1$–C$_{20}$-alkoxy, halogen, nitro, nitrile and C$_1$–C$_5$-acyl.

2. A pyridinium-TCNQ complex according to claim 1 wherein R represents an unsubstituted phenyl or naphthyl radical or a phenyl or naphthyl radical which is substituted by C$_1$–C$_4$-alkyl, C$_1$–C$_4$-alkoxy, halogen, or C$_1$–C$_5$-acyl.

* * * * *